(12) United States Patent
Lin et al.

(10) Patent No.: US 9,144,495 B2
(45) Date of Patent: Sep. 29, 2015

(54) STACK-UP ASSEMBLY FOR TIBIAL INSERT TRIAL

(71) Applicant: UNITED ORTHOPEDIC CORP., Hsinchu (TW)

(72) Inventors: Yan-Shen Lin, Hsinchu (TW); Ren-Hong Huang, Hsinchu (TW); Huang-Hsing Liu, Hsinchu (TW)

(73) Assignee: UNITED ORTHOPEDIC CORP., Hsinchu (TW)

( * ) Notice: Subject to any disclaimer, the term of this patent is extended or adjusted under 35 U.S.C. 154(b) by 0 days.

(21) Appl. No.: 14/297,497

(22) Filed: Jun. 5, 2014

(65) Prior Publication Data

US 2015/0238316 A1  Aug. 27, 2015

(30) Foreign Application Priority Data

Feb. 27, 2014 (TW) ............... 103203470 U

(51) Int. Cl.
*A61F 2/38* (2006.01)
*A61F 2/30* (2006.01)
*A61F 2/46* (2006.01)

(52) U.S. Cl.
CPC ............. *A61F 2/30734* (2013.01); *A61F 2/389* (2013.01); *A61F 2/4684* (2013.01); *A61F 2002/30599* (2013.01); *A61F 2002/30736* (2013.01)

(58) Field of Classification Search
CPC ......... A61F 2/4684; A61F 2/468; A61F 2/76; A61B 17/1675; A61B 17/025; A61B 2017/0268; A61B 2017/00544; A61B 17/157
USPC ................... 623/20.32, 20.34, 20.16; 606/88
See application file for complete search history.

(56) References Cited

U.S. PATENT DOCUMENTS

| | | | | |
|---|---|---|---|---|
| 5,019,103 A | * | 5/1991 | Van Zile et al. | 623/20.34 |
| 5,702,464 A | * | 12/1997 | Lackey et al. | 623/20.32 |
| 5,733,292 A | * | 3/1998 | Gustilo et al. | 606/88 |
| 5,928,286 A | * | 7/1999 | Ashby et al. | 623/20.33 |
| 6,102,954 A | * | 8/2000 | Albrektsson et al. | 623/20.32 |
| 6,214,052 B1 | * | 4/2001 | Burkinshaw | 623/20.34 |
| 7,309,363 B2 | * | 12/2007 | Dietz | 623/23.47 |
| 7,442,196 B2 | * | 10/2008 | Fisher et al. | 606/88 |
| 8,382,848 B2 | * | 2/2013 | Ries et al. | 623/20.29 |
| 8,591,594 B2 | * | 11/2013 | Parisi et al. | 623/20.32 |
| 8,613,775 B2 | * | 12/2013 | Wentorf et al. | 623/20.32 |
| 8,628,580 B2 | * | 1/2014 | Sanford et al. | 623/20.32 |
| 8,656,790 B2 | * | 2/2014 | Amirouche | 73/862.041 |
| 8,758,355 B2 | * | 6/2014 | Fisher et al. | 606/88 |
| 8,968,412 B2 | * | 3/2015 | Wogoman et al. | 623/20.15 |
| 2004/0225368 A1 | * | 11/2004 | Plumet et al. | 623/20.15 |
| 2004/0236429 A1 | * | 11/2004 | Ensign et al. | 623/20.32 |
| 2006/0111790 A1 | * | 5/2006 | Dietz | 623/20.32 |
| 2006/0184176 A1 | * | 8/2006 | Straszheim-Morley et al. | 606/88 |
| 2008/0051908 A1 | * | 2/2008 | Angibaud et al. | 623/20.32 |
| 2010/0010635 A1 | * | 1/2010 | Straszheim-Morley et al. | 623/20.32 |
| 2010/0217156 A1 | * | 8/2010 | Fisher et al. | 600/587 |

(Continued)

*Primary Examiner* — Alvin Stewart
(74) *Attorney, Agent, or Firm* — Vic Lin; Innovation Capital Law Group, LLP

(57) ABSTRACT

A stack-up assembly for tibial insert trial is provided. The stack-up assembly for tibial insert trial is inserted between a femoral component and a tibial component of an artificial knee joint. The stack-up assembly for tibial insert trial includes an insert trial body and a plurality of first augments. The insert body is operatively connected with the femoral component. The first augments are stacked between the tibial component and the insert trial body.

8 Claims, 4 Drawing Sheets

(56) References Cited

U.S. PATENT DOCUMENTS

| | | | |
|---|---|---|---|
| 2012/0022659 A1* | 1/2012 | Wentorf | 623/20.32 |
| 2012/0158152 A1* | 6/2012 | Claypool et al. | 623/20.33 |
| 2013/0006253 A1* | 1/2013 | Waite et al. | 606/88 |
| 2013/0006370 A1* | 1/2013 | Wogoman et al. | 623/20.16 |
| 2013/0006376 A1* | 1/2013 | Wogoman et al. | 623/20.32 |
| 2013/0006378 A1* | 1/2013 | Wogoman | 623/20.35 |
| 2013/0079668 A1* | 3/2013 | Stein et al. | 600/587 |
| 2013/0079671 A1* | 3/2013 | Stein et al. | 600/587 |
| 2013/0096567 A1* | 4/2013 | Fisher et al. | 606/102 |
| 2013/0173011 A1* | 7/2013 | Otto et al. | 623/20.32 |
| 2013/0261502 A1* | 10/2013 | Sherman et al. | 600/587 |
| 2013/0261505 A1* | 10/2013 | Sherman et al. | 600/595 |
| 2013/0261758 A1* | 10/2013 | Claypool et al. | 623/20.32 |
| 2013/0261759 A1* | 10/2013 | Claypool et al. | 623/20.33 |
| 2013/0325136 A1* | 12/2013 | Thomas et al. | 623/20.32 |
| 2014/0172112 A1* | 6/2014 | Marter | 623/20.32 |
| 2014/0243834 A1* | 8/2014 | Chaney et al. | 606/88 |
| 2014/0276857 A1* | 9/2014 | Major | 606/88 |
| 2014/0277539 A1* | 9/2014 | Cook et al. | 623/20.32 |
| 2014/0277546 A1* | 9/2014 | Major et al. | 623/20.33 |
| 2014/0296859 A1* | 10/2014 | Claypool et al. | 606/88 |
| 2014/0358242 A1* | 12/2014 | Mines | 623/20.32 |
| 2015/0057758 A1* | 2/2015 | Axelson et al. | 623/20.32 |
| 2015/0105782 A1* | 4/2015 | D'Lima et al. | 606/90 |

* cited by examiner

STACK-UP ASSEMBLY FOR TIBIAL INSERT TRIAL

RELATED APPLICATIONS

This application claims priority to Taiwan Application Serial Number 103203470, filed Feb. 27, 2014, which is herein incorporated by reference.

BACKGROUND OF THE INVENTION

1. Technical Field

The present invention relates to a stack-up assembly for tibial insert trial. More particularly, the present invention relates to a stack-up assembly for tibial insert trial of an artificial knee joint.

2. Description of Related Art

Artificial knee joints are used to cure patients with knee joint illnesses. However, due to the big difference in bone size for different patients, there should be a large number of artificial knee joints with different dimensions provided for different patients. In practice, due to different conditions of patients, the space at the knee of a patient provided for the implantation of an artificial knee joint cannot be accurately determined before operation. As a result, the traditional approach is to prepare a large number of insert trials, and then put the insert trials at the knee of the patient during an operation, so as to obtain the optimum dimensions for the particular patient. Finally, an implanting insert of corresponding dimensions is implanted into the artificial knee joint in the body of the patient.

However, the preparation of a large number of insert trials before each operation leads to an increase in cost, and also involves the inconvenience of transportation and storage. Moreover, the transportation of a large number of insert trials into an aseptically processed operating room will increase the risk and the workload of aseptic processing.

SUMMARY OF THE INVENTION

A technical aspect of the present invention provides a stack-up assembly for tibial insert trial which can reduce the space originally occupied by the large number of insert trials in the traditional approach.

According to an embodiment of the present invention, a stack-up assembly for tibial insert trial is provided. The stack-up assembly for tibial insert trial is inserted between a femoral component and a tibial component of an artificial knee joint. The stack-up assembly for tibial insert trial includes an insert trial body and a plurality of first augments. The insert trial body is operatively connected with the femoral component. The first augments are stacked between the tibial component and the insert trial body.

In one or more embodiments of the present invention, each of the first augments includes a first augment body, a plurality of first columns and a plurality of second columns. The first augment body has a first surface and a second surface opposite to each other. The first surface faces the insert trial body. The second surface faces the tibial component. The first columns are disposed on the first surface. Spaces between the first columns define a plurality of first sockets. The second columns are disposed on the second surface. The second columns are received in the first sockets of another first augment, such that the second columns and the first columns are snapped together and fixed to each other.

In one or more embodiments of the present invention, the insert trial body includes a load bearing part and a plurality of third columns. The load bearing part has a bottom surface. The bottom surface faces the tibial component. The third columns are disposed on the bottom surface. The third columns are received in the first sockets of the first augment abutting the insert trial body, such that the third columns and the first columns are snapped together and fixed to each other.

In one or more embodiments of the present invention, a shape and dimensions of each of the second columns are the same as a shape and dimensions of each of the third columns. An arrangement pattern of the second columns is the same as an arrangement pattern of the third columns.

In one or more embodiments of the present invention, the load bearing part has a first curved face and a second curved face. The first curved face and the second curved face face away from the tibial component. The stack-up assembly for tibial insert trial further includes a post. The post is removably connected to a side of the insert trial body facing away from the tibial component, and is located between the first curved face and the second curved face.

In one or more embodiments of the present invention, the stack-up assembly for tibial insert trial further includes a second augment. The second augment is disposed between the first augments and the tibial component. Each of the first augments has a first thickness. The second augment has a second thickness. The second thickness is thicker than the first thicknesses.

In one or more embodiments of the present invention, the second augment includes a second augment body and a plurality of fourth columns. The second augment body has a third face and a fourth face opposite to each other. The third surface faces the insert trial body. The fourth surface faces the tibial component. The fourth columns are disposed on the third surface. Spaces between the fourth columns define a plurality of second sockets, in which the second columns of the first augment abutting the second augment are received in the second sockets, such that the fourth columns and the second columns are snapped together and fixed to each other.

In one or more embodiments of the present invention, a shape and dimensions of each of the first columns are the same as a shape and dimensions of each of the fourth columns. An arrangement pattern of the first columns is the same as an arrangement pattern of the fourth columns.

In one or more embodiments of the present invention, a thickness of each of the first augments is the same.

BRIEF DESCRIPTION OF THE DRAWINGS

The invention can be more fully understood by reading the following detailed description of the embodiments, with reference made to the accompanying drawings as follows.

DETAILED DESCRIPTION OF THE INVENTION

Figure 1:
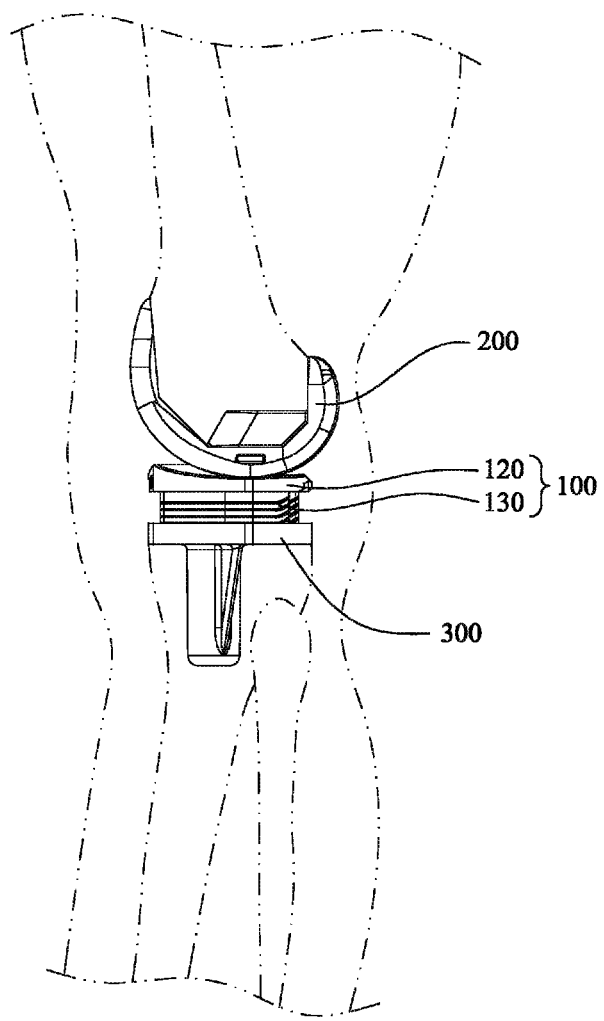
FIG. 1 is a schematic diagram of a stack-up assembly for tibial insert trial according to an embodiment of the present invention, illustrating the stack-up assembly for tibial insert in an implanted state.

Drawings will be used below to disclose a plurality of embodiments of the present invention. For the sake of clear illustration, many practical details will be explained together in the description below. However, it is appreciated that the practical details should not be used to limit the claimed scope. In other words, in some embodiments of the present invention, the practical details are not essential. Moreover, for the sake of drawing simplification, some customary structures and elements in the drawings will be schematically shown in a simplified way. Wherever possible, the same reference numbers are used in the drawings and the description to refer to the same or like parts.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

FIG. 1 is a schematic diagram of a stack-up assembly for tibial insert trial 100 according to an embodiment of the present invention, illustrating the stack-up assembly for tibial insert trial 100 in an implanted state. As shown in FIG. 1, the stack-up assembly for tibial insert trial 100 is inserted between a femoral component 200 and a tibial component 300 of an artificial knee joint, and includes an insert trial body 120 and a plurality of first augments 130. The femoral component 200 can be a femoral implant or a femoral trial, and the tibial component 300 can be a tibial implant or a tibial trial. In this embodiment, as shown in FIG. 1, the femoral component 200 is a femoral implant, and the tibial component 300 is a tibial implant. The femoral implant (i.e., the femoral component 200) is connected to the distal end of the femur of the patient, while the tibial implant (i.e., the tibial component 300) is connected to the proximal end of the tibia of the patient. The insert trial body 120 is operatively connected (i.e., slidably abutted) with the femoral implant (i.e., the femoral component 200). The first augments 130 are stacked between the tibial implant (i.e., the tibial component 300) and the insert trial body 120.

Figure 2:
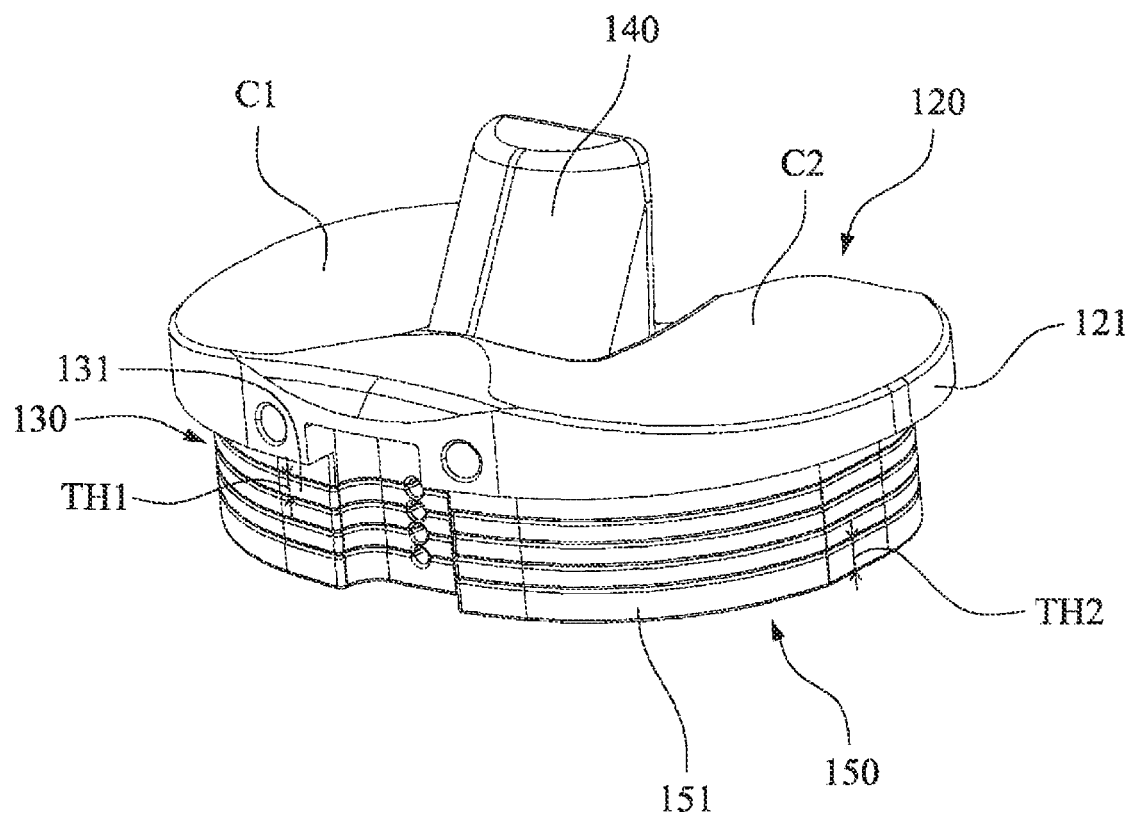
FIG. 2 is a perspective view of the stack-up assembly for tibial insert trial of FIG. 1.

As each patient requiring an artificial knee joint has a different bone size, the required overall thickness of the stack-up assembly for tibial insert trial 100 is also different from one patient to another. FIG. 2 is a perspective view of the stack-up assembly for tibial insert trial 100 of FIG. 1. In this embodiment, the number of the first augments 130 stacked between the tibial component 300 (see FIG. 1) and the insert trial body 120 is plural (i.e., more than one). Doctors can increase or decrease the number of the first augments 130 according to actual needs, so as to increase or decrease the overall thickness of the stack-up assembly for tibial insert trial 100.

Figure 3:
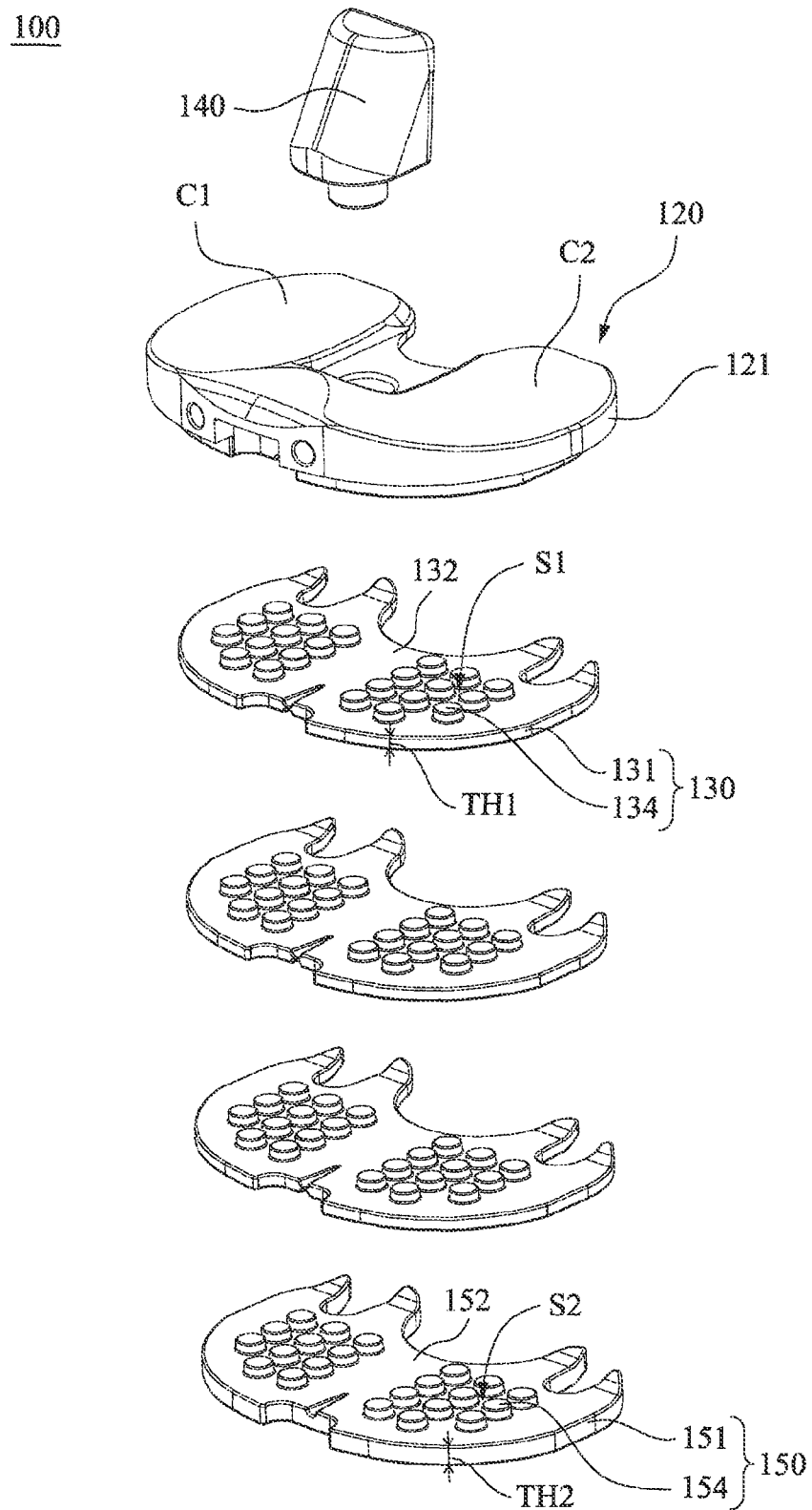
FIG. 3 is an exploded perspective view of the stack-up assembly for tibial insert trial of FIG. 1.
Figure 4:
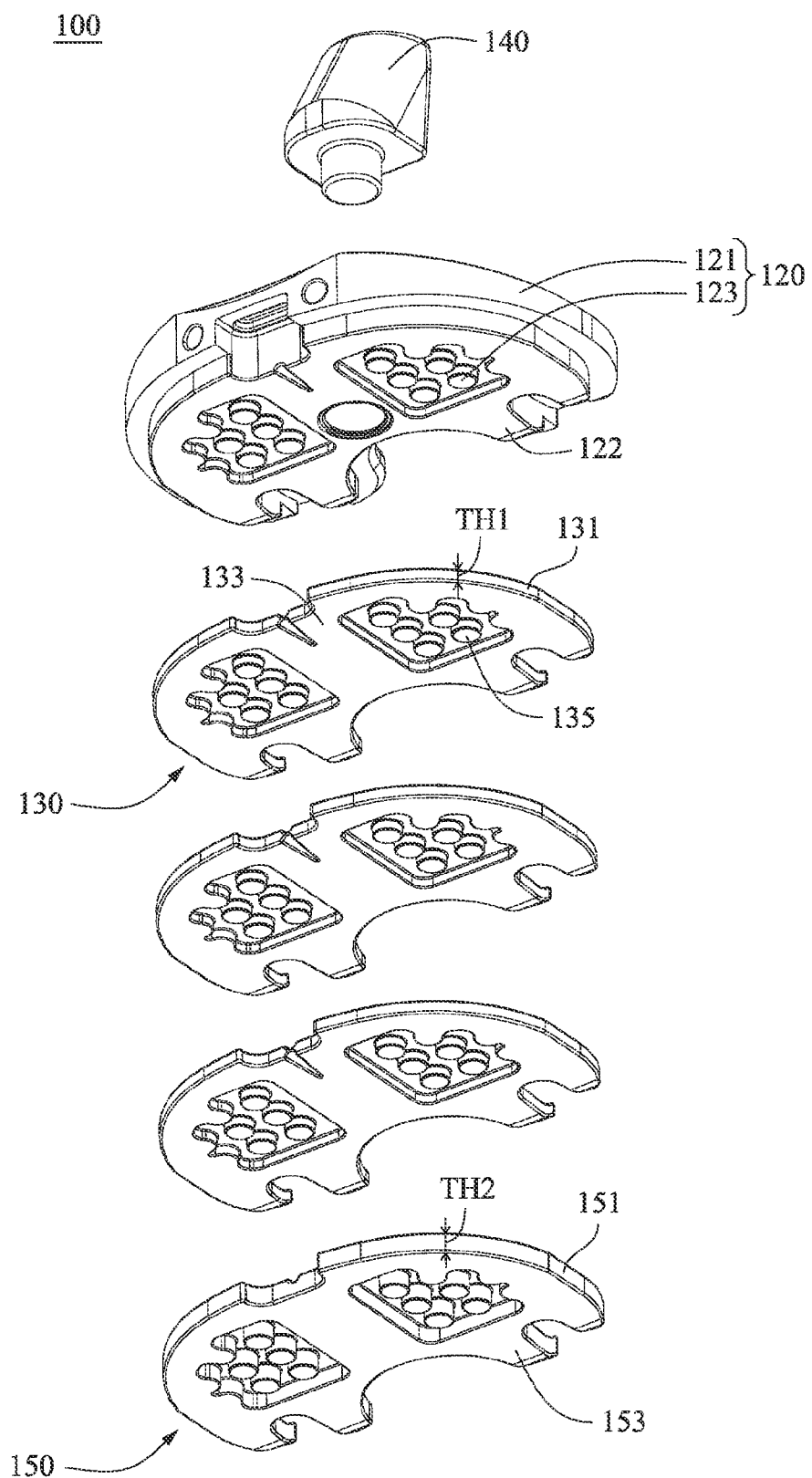
FIG. 4 is another exploded perspective view of the stack-up assembly for tibial insert trial of FIG. 1.

FIG. 3 is an exploded perspective view of the stack-up assembly for tibial insert trial 100 of FIG. 1. FIG. 4 is another exploded perspective view of the stack-up assembly for tibial insert trial 100 of FIG. 1. As shown in FIGS. 3 and 4, each of the first augments 130 includes a first augment body 131, a plurality of first columns 134 and a plurality of second columns 135. The first augment body 131 has a first surface 132 and a second surface 133 opposite to each other. The first surface 132 faces the insert trial body 120. The second surface 133 faces the tibial component 300 (see FIG. 1). The first columns 134 are disposed on the first surface 132. Spaces between the first columns 134 define a plurality of first sockets 51. The second columns 135 are disposed on the second surface 133. The second columns 135 are received in the first sockets 51 of another first augment 130, such that the second columns 135 of one of the first augments 130 and the first columns 134 of an adjacent one of the first augments 130 are snapped together and fixed to each other.

Through such receiving of the second columns 135 of one of the first augments 130 in the first sockets 51 of an adjacent one of the first augments 130 such that the second columns 135 and the first columns 134 are snapped together and fixed to each other, the relative positioning of the first augment 130 and the adjacent first augment 130 can be fixed. By accurately controlling the dimensions and tolerances of the first columns 134 and the second columns 135 during manufacture, the second columns 135 of the first augment 130 and the first columns 134 of the adjacent first augment 130 can be snapped together and firmly fixed to each other. As a result, the first augment 130 and the adjacent first augment 130 will not be easily separated after such snapping and fixing respectively of the second columns 135 and the first columns 134 thereof.

As shown in FIG. 4, the insert trial body 120 includes a load bearing part 121 and a plurality of third columns 123. The load bearing part 121 has a bottom surface 122. The bottom surface 122 faces the tibial component 300 (see FIG. 1).

The third columns 123 are disposed on the bottom surface 122. The third columns 123 are received in the first sockets S1 of the first augment 130 abutting the insert trial body 120, such that the third columns 123 of the insert trial body 120 and the first columns 134 of the adjacent first augment 130 are snapped together and fixed to each other.

Through such receiving of the third columns 123 of the insert trial body 120 in the first sockets S1 of the first augment 130 abutting the insert trial body 120 such that the third columns 123 and the first columns 134 are snapped together and fixed to each other, the relative positioning of the insert trial body 120 and the first augment 130 abutting the insert trial body 120 can be fixed. By accurately controlling the dimensions and tolerances of the first columns 134 and the third columns 123 during manufacture, the third columns 123 of the insert trial body 120 and the first columns 134 of the first augment 130 abutting the insert trial body 120 can be snapped together and firmly fixed to each other. As a result, the insert trial body 120 and the first augment 130 abutting the insert trial body 120 will not be easily separated after such snapping and fixing respectively of the third columns 123 and the first columns 134 thereof.

Furthermore, the shape and the dimensions of the second columns 135 are the same as the shape and the dimensions of the third columns 123. Additionally, the arrangement pattern of the second columns 135 is the same as the arrangement pattern of the third columns 123. Therefore, the second columns 135 of any one of the first augments 130 can be received in the first sockets S1 of an adjacent one of the first augments 130, and the third columns 123 of the insert trial body 120 can also be received in the first sockets S1 of the first augment 130 abutting the insert trial body 120. As a result, by the consistency in the shape and the dimensions of the second columns 135 and the third columns 123, the number of the first augments 130 stacked between the tibial component 300 (see FIG. 1) and the insert trial body 120 can be simply increased or decreased according to actual needs.

As shown in FIGS. 2 and 3, the load bearing part 121 has a first curved face C1 and a second curved face C2. The first curved face C1 and the second curved face C2 face away from the tibial component 300 (see FIG. 1). The first curved face C1 and the second curved face C2 abut against the femoral component 200 (see FIG. 1), allowing relative sliding between the femoral component 200 and the insert trial body 120. The stack-up assembly for tibial insert trial 100 further includes a post 140. The post 140 is removably connected to a side of the insert trial body 120 facing away from the tibial component 300 (see FIG. 1), and is located between the first curved face C1 and the second curved face C2.

During the process of implanting an artificial knee joint, a doctor may cut off the posterior cruciate ligament of a patient and implant an artificial knee joint of posterior-stabilized type (PS Type) into the body of the patient. When the artificial knee joint of PS Type is used, the post 140 is used with the stack-up assembly for tibial insert trial 100, such that the thickness of the stack-up assembly for tibial insert trial 100 can be correctly tested for the artificial knee joint of PS Type.

In contrast, a doctor may retain the posterior cruciate ligament of a patient and implant an artificial knee joint of posterior cruciate ligament-retaining type (CR Type) into the body of the patient. When the artificial knee joint of CR Type is used, the post 140 is not used with the stack-up assembly for tibial insert trial 100, such that the thickness of the stack-up assembly for tibial insert trial 100 can be correctly tested for the artificial knee joint of CR Type.

In the aseptically processed operating room, assembly and disassembly of the first augments 130 are simple and easy. As explained above, the process of installing the first augments 130 to the stack-up assembly for tibial insert trial 100 involves a snapping operation which is simple and easy.

In order to further increase the flexibility of the thickness adjustment of the stack-up assembly for tibial insert trial 100, as shown in FIGS. 2-4, the stack-up assembly for tibial insert trial 100 further includes a second augment 150. The second augment 150 is disposed between the first augments 130 and the tibial component 300 (see FIG. 1). Each of the first augments 130 has a first thickness TH1. The second augment 150 has a second thickness TH2. The second thickness TH2 is thicker than the first thicknesses TH1.

As shown in FIGS. 3 and 4, the second augment 150 includes a second augment body 151 and a plurality of fourth columns 154. The second augment body 151 has a third face 152 and a fourth face 153 opposite to each other. The third surface 152 faces the insert trial body 120. The fourth surface 153 faces the tibial component 300 (see FIG. 1). The fourth columns 154 are disposed on the third surface 152. Spaces between the fourth columns 154 define a plurality of second sockets S2, in which the second columns 135 of the first augment 130 abutting the second augment 150 are received in the second sockets S2, such that the fourth columns 154 and the second columns 135 respectively of the second augment 150 and the adjacent first augment 130 are snapped together and fixed to each other.

Furthermore, the shape and the dimensions of the first columns 134 are the same as the shape and the dimensions of the fourth columns 154. Additionally, the arrangement pattern of the first columns 134 is the same as the arrangement pattern of the fourth columns 154. Therefore, the second columns 135 of any one of the first augments 130 can be received in the first sockets 51 of an adjacent one of the first augments 130, and also can be received in the second sockets S2 of the second augment 150. As a result, by the consistency in the shape and the dimensions of the first columns 134 and the fourth columns 154, the number of the first augments 130 stacked between the tibial component 300 (see FIG. 1) and the insert trial body 120 can be simply increased or decreased according to actual needs.

For the sake of consistency, the first thicknesses TH1 of the first augments 130 are the same. In this embodiment, the range of the first thicknesses TH1 of the first augments 130 is from 1.5 mm to 5 mm. It is noted that the first thicknesses TH1 of the first augments 130 as cited herein are only illustrative and are not to limit the claimed scope. A person having ordinary skill in the art of the present invention may flexibly choose the first thicknesses TH1 of the first augments 130 depending on actual needs.

Additionally, in this embodiment, the range of the second thickness TH2 of the second augment 150 is also from 1.5 mm to 5 mm. However, as mentioned above, the second thickness TH2 of the second augment 150 is thicker than the first thicknesses TH1 of the first augments 130. Thus, for example, if the first thicknesses TH1 of the first augments 130 are 2 mm, the second thickness TH2 of the second augment 150 can be 3 mm, and it is necessary only that the second thickness TH2 be thicker than the first thicknesses TH1. It is noted that the second thickness TH2 of the second augment 150 as cited herein is only illustrative and is not to limit the claimed scope. A person having ordinary skill in the art of the present invention may flexibly choose the second thickness TH2 of the second augment 150 depending on actual needs.

In summary, when compared with the prior art, the embodiments of the present invention mentioned above have at least the following advantages:

(1) In the embodiments of the present invention, a plurality of the first augments is stacked between the tibial component and the insert trial body. Therefore, by increasing the number of the first augments stacked, the overall thickness of the stack-up assembly for tibial insert trial can be adjusted.

(2) In the embodiments of the present invention, the second augment is disposed between the first augments and the tibial component, and the second thickness of the second augment is thicker than the first thicknesses of the first augments. Therefore, the overall thickness of the stack-up assembly for tibial insert trial can be more flexibly varied when combined.

(3) Since the post is removably connected to the insert trial body, doctors have the flexibility of determining whether the stack-up assembly for tibial insert trial should include the post, depending on the actual needs of each operation.

Although the present invention has been described in considerable detail with reference to certain embodiments thereof, other embodiments are possible. Therefore, the spirit and scope of the appended claims should not be limited to the description of the embodiments contained herein.

It will be apparent to the person having ordinary skill in the art that various modifications and variations can be made to the structure of the present invention without departing from the scope or spirit of the present invention. In view of the foregoing, it is intended that the present invention cover modifications and variations of the present invention provided they fall within the scope of the following claims.

What is claimed is:

1. A stack-up assembly for tibial insert trial inserted between a femoral component and a tibial component of an artificial knee joint, the stack-up assembly for tibial insert trial comprising:

an insert trial body operatively connected with the femoral component; and a plurality of first augments stacked between the tibial component and the insert trial body, wherein each of the first augments comprises:

a first augment body having a first surface and a second surface opposite to each other, the first surface facing the insert trial body, the second surface facing the tibial component;

a plurality of first columns disposed on the first surface, spaces between the first columns defining a plurality of first sockets; and a plurality of second columns disposed on the second surface, the second columns being received in the first sockets of another first augment, such that the second columns and the first columns of another first augment are snapped together and fixed to each other.

2. The stack-up assembly for tibial insert trial of claim 1, wherein the insert trial body comprises:
   a load bearing part having a bottom surface, the bottom surface facing the tibial component; and
   a plurality of third columns disposed on the bottom surface, the third columns being received in the first sockets of the first augment abutting the insert trial body, such that the third columns and the first columns are snapped together and fixed to each other.

3. The stack-up assembly for tibial insert trial of claim 2, wherein a shape and dimensions of each of the second columns are the same as a shape and dimensions of each of the third columns, and an arrangement pattern of the second columns is the same as an arrangement pattern of the third columns.

4. The stack-up assembly for tibial insert trial of claim 2, wherein the load bearing part has a first curved face and a second curved face, the first curved face and the second curved face facing away from the tibial component, the stack-up assembly for tibial insert trial further comprising:
   a post removably connected to a side of the insert trial body facing away from the tibial component, and located between the first curved face and the second curved face.

5. The stack-up assembly for tibial insert trial of claim 1, further comprising:
   a second augment disposed between the first augments and the tibial component, each of the first augments having a first thickness, the second augment having a second thickness, the second thickness being thicker than the first thicknesses.

6. The stack-up assembly for tibial insert trial of claim 5, wherein the second augment comprises:
   a second augment body having a third face and a fourth face opposite to each other, the third surface facing the insert trial body, the fourth surface facing the tibial component; and
   a plurality of fourth columns disposed on the third surface, spaces between the fourth columns defining a plurality of second sockets, wherein the second columns of the first augment abutting the second augment are received in the second sockets, such that the fourth columns and the second columns are snapped together and fixed to each other.

7. The stack-up assembly for tibial insert trial of claim 6, wherein a shape and dimensions of each of the first columns are the same as a shape and dimensions of each of the fourth columns, and an arrangement pattern of the first columns is the same as an arrangement pattern of the fourth columns.

8. The stack-up assembly for tibial insert trial of claim 1, wherein a thickness of each of the first augments is the same.

* * * * *